(12) United States Patent
Örçen

(10) Patent No.: US 12,194,069 B2
(45) Date of Patent: Jan. 14, 2025

(54) USE OF PROBIOTIC YEAST CELLS PRODUCING RECOMBINANT PARATHORMONE FOR THERAPEUTIC PURPOSES

(71) Applicant: Arda Örçen, Istanbul (TR)

(72) Inventor: Arda Örçen, Istanbul (TR)

(73) Assignee: NANOMIK BIYOTEKNOLOJI ANONIM SIRKETI, Istanbul (TR)

( * ) Notice: Subject to any disclaimer, the term of this patent is extended or adjusted under 35 U.S.C. 154(b) by 299 days.

(21) Appl. No.: 17/296,308

(22) PCT Filed: Dec. 4, 2018

(86) PCT No.: PCT/TR2018/050758
§ 371 (c)(1),
(2) Date: May 24, 2021

(87) PCT Pub. No.: WO2020/106234
PCT Pub. Date: May 28, 2020

(65) Prior Publication Data
US 2022/0370528 A1    Nov. 24, 2022

(30) Foreign Application Priority Data
Nov. 22, 2018   (TR) .................................. 2018/17691

(51) Int. Cl.
*A61K 36/064* (2006.01)
*A61K 38/29* (2006.01)
*C12N 1/18* (2006.01)

(52) U.S. Cl.
CPC ............ *A61K 36/064* (2013.01); *A61K 38/29* (2013.01); *C12N 1/185* (2021.05)

(58) Field of Classification Search
None
See application file for complete search history.

(56) References Cited

U.S. PATENT DOCUMENTS

| 2011/0059164 A1 | 3/2011 | Hendrickson et al. |
| 2011/0172826 A1* | 7/2011 | Amodei .................. C12N 1/36 700/266 |

OTHER PUBLICATIONS

Hamedi et al. "Generation of a Uracil Auxotroph Strain of the Probiotic Yeast *Saccharomyces boulardii* as a Host for the Recombinant Protein Production". Avecena Journal of Medical Biotechnology. 2013, 5(1), pp. 29-34.*
Liu et al. Scientific Reports, May 2017, 7: 2193, pp. 1-9.*
Min Wu et al. J Ind Microbiol Biotechnol, 2013, 40, pp. 589-599.*
Lin-Cereghino et al. Gene, 2013, 519, pp. 311-317.*
Mortazavian et al. "Principles and methods of microencapsulation of probiotic microorganisms", Iranian Journal of Biotechnology, 2007, vol. 5, No. 1, pp. 1-18.*
International Search Report of PCT/TR2018/050758, Mailed On Feb. 19, 2020.

* cited by examiner

*Primary Examiner* — Vera Afremova
(74) *Attorney, Agent, or Firm* — Bayramoglu Law Offices LLC

(57) ABSTRACT

This invention relates to the use of probiotic yeast cells that produce recombinant parathormone for therapeutic purposes, where probiotic cells that produce rhPTH developed for use in hypoparathyroidism treatment are first microencapsulated, placed into gelatin capsules and then orally administrated.

5 Claims, No Drawings
Specification includes a Sequence Listing.

USE OF PROBIOTIC YEAST CELLS PRODUCING RECOMBINANT PARATHORMONE FOR THERAPEUTIC PURPOSES

TECHNICAL FIELD

This invention relates to the use of probiotic yeast cells that produce recombinant parathormone for therapeutic purposes, where probiotic cells that produce rhPTH developed for use in hypoparathyroidism treatment are first microencapsulated, placed into gelatin capsules and then orally administrated.

BACKGROUND OF THE INVENTION

Hypoparathyroidism is a congenital or developmental disease. Most frequently, it appears as a complication of thyroid operations. In respect of patients who underwent a thyroid surgical operation, the temporary hypoparathyroidism frequency is 10-30% while the permanent hypoparathyroidism (PH) frequency is 1-3%. Today's treatment approach is giving vitamin D and calcium preparations for lifetime. The best alternative to the PH treatment is the use of recombinant human parathormone (rhPTH).

If used in an appropriate amount, probiotics are defined as viable microorganisms such as bacteria and yeasts that are useful for the host health, that could remain alive in intestines and, that are resistant to digestion. *Saccharomyces boulardii* is a probiotic microorganism and antidiaretic, and used for therapeutic purposes. It has no side-effect to human health. Since it is a eukaryotic microorganism in respect of protein production, it can make posttranslational modifications and, ensures the production of complex proteins.

According to the state of the art, rhPTH needs to be continuously used by patients for the hypoparathyroidism treatment. The fact that it requires injections continuously and the price of these medications are too high makes the PH treatment difficult.

There is no another invention in relation with the hormone replacement or hypoparathyroidism treatment with *Saccharomyces boulardii* cells that produce recombinant parathormone or another hormone, which directly affects the invention. However, there are two patents through which specific molecules are produced for therapeutic purposes by means of use of *Saccharomyces boulardii* yeast cells. The invention publication number WO 2007/039586 relates to the production by *Saccharomyces boulardii* of interleukin 10 (IL10), tumor necrosis factor (TNF) molecules and trefoil factors as recombinants for use in the treatment of inflammatory bowel diseases (ulcerative colitis, Crohn's disease etc.). The invention publication number WO 2016/073562 relates to the production by *Saccharomyces boulardii* cells of neutralizing antibodies.

The invention has been developed to overcome the problems in the current technique and relates to use of probiotic *Saccharomyces boulardii* cells as a live drug delivery system. The capsules containing recombinant *Saccharomyces boulardii* cells may be used for the permanent hypoparathyroidism treatment.

In this invention, *Saccharomyces boulardii* yeast that produce rhPTH settle in the gastrointestinal system and hold on in this site, living and continuing to produce. In case of deficiency, it is possible to deliver it again orally or rectally without the need for any surgical intervention. It provides far less application for the PH compared to injectable (intravenous, subcutaneous, intradermal etc.).

DESCRIPTION OF THE INVENTION

This detailed description relates to the use of probiotic yeast cells that produce recombinant parathormone for therapeutic purposes and is hereby presented as follows in a manner not to create any limiting effect in understanding this matter in a better way.

*Saccharomyces boulardii* cells should go through various phases for the use of probiotic yeast cells that produce recombinant parathormone for therapeutic purposes. Here are these phases:

- Making *Saccharomyces boulardii* cells URA3, HIS3, TRP1, ADE1, ADE2, CAN1 and LEU2 auxotroph in the existence of gRNA's (Guide RNA's) developed by means of a CRISPR/Cas9, UV mutagenesis or Cre-lox recombination system;
- Creation of a gRNA (Guide RNA) targeting URA3, HIS3, TRP1, ADE1, ADE2, CAN1 and LEU2 in *Saccharomyces boulardii* genome and, placement of these Guide RNA's together with an appropriate promotor and terminator into a Euroscarf (no: P30636) plasmid (pRS42H) that contains an antibiotic resistance gene
- Placement of gene sequence that codes spCas9 protein together with an appropriate promotor and terminator into an Addgene (no: 43802) plasmid (p414-TEF1p-Cas9-CYC1t) that contains an antibiotic resistance gene,
- Creation of yeast expression cassette and plasmid that contain human parathormone gene (pYES1, pYES2 or pSF-URA3) (Thermo-Scientific (no: V82520), Oxford Genetics (OG534))
- Culture, transformation and selection of *Saccharomyces boulardii* cells
- Measurement of parathormone produced by *Saccharomyces boulardii* cells extracellularly in a liquid culture,
- Microencapsulation of *Saccharomyces boulardii* cells that produce recombinant parathyroid hormones in CFU cell concentrations of $3\times10^1$, $10^2$, $10^3$, $10^4$, $10^5$, $10^6$, $10^7$, $10^8$, $10^9$, $10^{10}$, $10^{11}$, $10^{12}$, $10^{13}$ and, then placement thereof into gelatin capsules.

In order to make *Saccharomyces boulardii* cells URA3 auxotroph by means of CRISPR/Cas9 (a gene editing tool):

- *Saccharomyces boulardii* forms a double stranded cut with a spCas9 enzyme codon optimized according to human genome and guide RNA (gRNA) created in accordance with 804-base farm URA3 gene available in the 5th chromosome in the cells after they are taken from a commercial probiotic mixture or by means of the product code no. MYA-796 from ATCC.
- 90-base donor DNA formed in this manner is replaced with this area where a cut is formed.
- With this replacement in an area close to the 5' end of URA3 ORF, an early phase stop codon is formed.
- In this manner, URA3 gene is inactivated and, consequently an auxotrophic cell line is formed.
- In order to form URA-3 targeted gRNA:
- SNR52 premotor and SUP4 terminator are used for gRNA expression,
- This SNR52-guide is reproduced with primers formed with URA3 RNA-SUP4,
- By this means, Sac I and Kpn I enzyme cutting sites are placed at the beginning and end of the DNA sequence, pRS42H plasmid where gRNA is to be cloned is cut with the same enzymes and, these two parts are attached with a bonding procedure, However, 30 bases of the 90-base donor DNA that is to be added to the sequence by means of homologues recombination after the double chain brake is formed contain the selected PAM and targeted gRNA site.

And the remaining 60 bases contain homologues sites to the URA3 gene in a manner where 30 bases are on the right side and 30 bases are on the left side.

Cas9 enzyme recognizes the appropriate PAM (protospacer adjacent motif) sequence boated in front of the 20-base single chain guide RNA site from the "CCG" sequence, is attached thereto and, cuts before the first cytosine nucleotide.

With the attachment of the CCG donor DNA located after the T/CCG Thymine nucleotide located in front of this site that is cut, it turns into a stop codon (TAA) and the URA3 gene is inactivated with the early phase stop codon.

In order to form the human parathormone expression cassette:

Since the green fluorescent protein (GFP) is used as an intracellular marker in the production of rhPTH; a cassette is formed that is to be divided into two pieces in ribosome by means of creating the same mRNA transcript, 34 amino acid human parathormone (PTH) gene and GFP gene are produced as bicistronic mRNA (messenger RNA that contains two ribosome attachment site) in the form of fusion with 2A peptide that can be divided on the ribosome by means of folding on itself.

This sequence is prepared as a synthetic gene sequence and, Sac I and Not I enzyme cutting site is placed at the begging and end of the sequence.

By this means, it is cloned to the pSF-URA3 plasmid,

Further, with the MF-alpha signal sequence to be added to the 5' part of the PTH gene, the cells may excrete the PTH peptide into an extracellular media.

rhPTH is also produced in a the form of fusion with HSA (Human Serum Albumin) protein or OVA (ovalbumin) protein, These fusion accompanying proteins protect the parathyroid hormone from being enzymatically disruption for a longer period of time, With fusion protein it is aimed to extend the PTH's half-life in the blood and protect it from proteolytic disruption and, this fusion protein is cut from the Sac I and Not I enzyme cutting sites and, cloned into the pSF-URA3 plasmid.

For the culture, transformation and selection of *Saccharomyces boulardii* cells:

Saccharomyces boulardii cells are first planted into the YPD (Yeast Extract Peptone Dextrose) medium (10 g/L of yeast extract, 20 g/L of peptone and 20 g/L of dextrose) and cultured at 30° C., Thereafter, the colonies are taken to the broth YPD medium and, cultured for 2 days until it reaches OD 600: 0.5-1.

After the appropriate concentration is reached, the cells are taken and, plasmids (Cas9-NAT 1 µg, pRS42H-guide RNA URA3 1 µg) and donor DNA (4 µg) are transformed into cells according to the Polyethyleneglycol/Lithium/Sorbitol acetate protocol, After the transformation, the cells are planted into the YPD medium that contains suitable antibiotics (hygromycin 300 µg/ml, nourseothricin 100 µg/ml), Positive colonies are selected and taken into the growing YPD broth medium, In addition, the yeast cells that are URA3 inactivated are selected in the 5-FOA (fluoroorotic acid) opposite selection medium.

For the measurement of parathormone produced by *Saccharomyces boulardii* cells extracellularly in a liquid culture:

While they are growing in the YPD broth medium, the yeast cells continuously express the PTH-2A-GFP cassette in the presence of the TEF1 promotor, PTH peptide is taken to an extracellular medium due to the MF-alpha secretion signal molecule at the N terminal end, Yeast cells are expressed at 30° C. for 3 days, then taken from the culture and, centrifuged at 5000 rpm for 7 minutes, Thereafter, the supernatant liquid is taken, centrifuged at 1500 rpm for 5 minutes and sedimented, From the supernatant liquid obtained, PTH is quantified by means of the Enzyme Linked Immunosorbent Assay (ELISA), At the same time, the protein quantification is done by means of the bicinchoninic acid assay (BCA) method and, the presence of the hormone is verified with the sodium dodecyl sulfate polyacrylamide gel electrophoresis (SDS-PAGE), Thereafter, it is distilled with affinity and size column chromatography and, the N-terminal Mass Spectroscopy and Western-Blot test are performed.

After all the procedure steps, *Saccharomyces boulardii* cells that produce recombinant parathyroid hormones are microencapsulated in CFU cell concentrations of $3 \times 10^1$, $10^2$, $10^3$, $10^4$, $10^5$, $10^6$, 107, $10^8$, $10^9$, $10^{10}$, $10^{11}$, $10^{12}$, $10^{13}$ and, then placed into gelatin capsules. To do that:

Saccharomyces boulardii cells grown at the YPD medium is sedimented by means of centrifuge, 1% of sodium alginate is mixed with 0.05% of inulin, 0.05% of trehalose and 0.05% of mucilage and, 0.5% of CaCO3 is added, At the same time, as another mixture, 200 ml of canola oil is mixed with 2.5 ml of Tween 80, Thereafter, the mixture that contains *Saccharomyces boulardii* cells is mixed with the other oil mixture in a magnetic mixture for 20 minutes, The capsules formed are washed with 200 ml of distilled water, Microcapsules are frozen at −20° C. for 5 hours, Thereafter, they are placed in a refrigerated dryer and, pressurized with 3 mm Hg and, the samples are dried at 20° C. for 24 hours.

The technical features and all other features mentioned in each claim are follows by the reference numbers, which are used only to facilitate the understanding of the claims, therefore it should not be considered that the procedure steps indicated by these reference numbers for the purpose of sampling limit the respective scope.

It is obvious that a person specialized about the technique may reveal the innovation specified in this invention by means of using similar structures and/or implements this structure in other areas with similar purposes used in the respective technique. Therefore, it is also obvious that such structures would lack of innovation and, in particular, the criterion to exceed the known condition of the technique.

What is claimed is:

1. A method for producing probiotic yeast cells as a live drug delivery system for the treatment of permanent hypoparathyroidism comprising the following steps:
   a) producing a URA3 auxotroph *Saccharomyces boulardii* cell strain by UV mutagenesis;
   b) creating a plasmid comprising SEQ ID NO: 8, wherein step (b) comprises the steps of:
   b-i) producing a bicistronic mRNA comprising a UKG fluorescent protein gene and a gene expressing an active 34 N-terminal amino acids of rhPTH in the form of fusion with 2A peptide;
   b-ii) adding an MF-alpha signal sequence to the 5' end of the rhPTH gene from step (b-i);
   b-iii) preparing a synthetic gene sequence from the bicistronic mRNA of step (b-ii), wherein a Sac I and Not I enzyme cutting site is placed at the beginning and end of the sequence to obtain the sequence SEQ ID NO: 8; and
   b-iv) cloning the sequence from step (b-iii) into a pSF-URA3 plasmid to obtain a pSF-URA3-fusion protein plasmid;
   c) transforming the URA3 auxotroph *Saccharomyces boulardii* cells from step (a) with the pSF-URA3-fusion protein plasmid from step (b), selecting for *Saccharomyces boulardii* cells that produce a rhPTH, culturing the recombinant *Saccharomyces boulardii* cells in a liquid culture medium, and producing a recombinant *Saccharomyces boulardii* cell culture;
   d) measuring the rhPTH secreted by the recombinant *Saccharomyces boulardii* cell culture taken from the liquid culture medium from step (c);
   e) microencapsulating the recombinant *Saccharomyces boulardii* cells that produce the rhPTH; and
   f) placing the microencapsulated recombinant *Saccharomyces boulardii* cells into a gelatin capsule suitable for oral administration, wherein each gelatin capsule comprises between 30 and $1 \times 10^{13}$ CFU of the recombinant *Saccharomyces boulardii* cells.

2. The method according to claim 1, wherein step (c) comprises the following steps:
   c-i) planting the URA3 auxotroph *Saccharomyces boulardii* cells from step (a) on to a Yeast Extract Peptone Dextrose (YPD) solid medium at 10 g/L of yeast extract, 20 g/L of peptone and 20 g/L of dextrose and culturing at 30° C. forming colonies of URA3 auxotroph *Saccharomyces boulardii*,
   c-ii) taking the URA3 auxotroph *Saccharomyces boulardii* colonies to a YPD liquid medium and, culturing for 2 days until a concentration reaches OD 600:0.5-1;
   c-iii) taking the URA3 auxotroph *Saccharomyces boulardii* cells from step (c-ii) and, transforming the pSF-URA3-fusion protein plasmid into the URA3 auxotroph *Saccharomyces boulardii* cells according to the Polyethyleneglycol/Lithium/Sorbitol acetate protocol;
   c-iv) planting the transformed cells from step (c-iii) into the Uracil (−) minimal agar plate after the transformation forming transformed colonies;
   c-v) selecting the transformed colonies and growing the cells from step (c-iv) in YPD medium; and
   c-vi) verifying that the yeast cells from step (c-v) are URA3 inactivated by culturing in a medium comprising 5-FOA (fluoroorotic acid).

3. The method according to claim 1, wherein step (d) comprises the following steps:
   d-i) growing the recombinant *Saccharomyces boulardii* cell culture expressing rhPTH from step (c) in a YPD medium at 30° C. for 3 days, then taking a sample from the culture medium and, centrifuging at 5000 rpm for 7 minutes;
   d-ii) taking a first supernatant liquid, centrifuging at 1500 rpm for 5 minutes and sedimenting;
   d-iii) obtaining a second supernatant liquid containing extracellular rhPTH;
   d-iv) quantifying the amount of rhPTH by one or more of the following methods: an Enzyme Linked Immunosorbent Assay (ELISA),
   a bicinchoninic acid assay (BCA), sodium dodecyl sulfate polyacrylamide gel electrophoresis (SDS-PAGE) followed by a Western-Blot assay, or
   performing affinity and size column chromatography and N-terminal Mass Spectroscopy.

4. The method according to claim 1, wherein step (e) comprises the following steps:
   e-i) growing the recombinant *Saccharomyces boulardii* cell culture expressing rhPTH from step (c) in a YPD medium until a concentration reaches OD 600:0.5-1;

e-ii) sedimenting the cell culture medium by means of centrifuge;

e-iii) mixing 1% of sodium alginate with 0.05% of inulin, 0.05% of trehalose and 0.05% of mucilage and, 0.5% of $CaCO_3$ and adding to the sediment from step (e-ii);

e-iv) mixing 200 ml of canola oil with 2.5 ml of Tween 80 producing an oil mixture;

e-v) mixing a mixture that contains *Saccharomyces boulardii* cells from step (e-iii) with the oil mixture from step (e-iv) with a magnetic stirrer for 20 minutes to form microcapsules;

e-vi) washing the microcapsules formed with 200 ml of distilled water;

e-vii) freezing the microcapsules at −20° C. for 5 hours; and e-viii) placing said microcapsules in a refrigerated dryer, pressurized at 3 mm Hg and, drying at 20° C. for 24 hours.

5. The method according to claim 2, wherein in step (c-i) the Yeast Extract Peptone Dextrose (YPD) solid medium includes agar.

\* \* \* \* \*

SEQUENCE LISTING

<160> NUMBER OF SEQ ID NOS: 9

<210> SEQ ID NO 1
<211> LENGTH: 4140
<212> TYPE: DNA
<213> ORGANISM: Artificial Sequence
<220> FEATURE:
<223> OTHER INFORMATION: fusion of Cas9 sequence from Streptococcus
      pyogenes with nuclear localization signal from Simian virus 40
<220> FEATURE:
<221> NAME/KEY: CDS
<222> LOCATION: (1)..(6)

<400> SEQUENCE: 1

```
atg gac aagaagtact ccattgggct cgatatcggc acaaacagcg tcggttgggc        56
Met Asp
1 cgtcattacg gacgagtaca aggtgccgag caaaaaattc aaagttctgg caataccga     116 tcgccacagc ataaagaaga acctcattgg cgccctcctg ttcgactccg gggagacggc    176 cgaagccacg cggctcaaaa gaacagcacg gcgcagatat acccgcagaa agaatcggat    236 ctgctacctg caggagatct ttagtaatga gatggctaag gtggatgact ctttcttcca    296 taggctggag gagtcctttt tggtggagga ggataaaaag cacgagcgcc acccaatctt    356 tggcaatatc gtggacgagg tggcgtacca tgaaaagtac ccaaccatat atcatctgag    416 gaagaagctt gtagacagta ctgataaggc tgacttgcgg ttgatctatc tcgcgctggc    476 gcatatgatc aaatttcggg gacacttcct catcgagggg gacctgaacc cagacaacag    536 cgatgtcgac aaactcttta tccaactggt tcagacttac aatcagcttt tcgaagagaa    596 cccgatcaac gcatccggag ttgacgccaa agcaatcctg agcgctaggc tgtccaaatc    656 ccggcggctc gaaaacctca tcgcacagct ccctggggag aagaagaacg gcctgtttgg    716 taatcttatc gccctgtcac tcgggctgac ccccaacttt aaatctaact tcgacctggc    776 cgaagatgcc aagcttcaac tgagcaaaga cacctacgat gatgatctcg acaatctgct    836 ggcccagatc ggcgaccagt acgcagacct ttttttggcg gcaaagaacc tgtcagacgc    896 cattctgctg agtgatattc tgcgagtgaa cacggagatc accaaagctc cgctgagcgc    956 tagtatgatc aagcgctatg atgagcacca ccaagacttg actttgctga aggcccttgt   1016 cagacagcaa ctgcctgaga gtacaaagga aattttcttc gatcagtcta aaaatggcta   1076 cgccggatac attgacggcg agcaagcca ggaggaattt tacaaattta ttaagcccat    1136 cttggaaaaa atggacggca ccgaggagct gctggtaaag cttaacagag aagatctgtt   1196 gcgcaaacag cgcactttcg acaatggaag catcccccac cagattcacc tgggcgaact   1256 gcacgctatc ctcaggcggc aagaggattt ctaccccttt ttgaaagata cagggaaaa    1316 gattgagaaa atcctcacat ttcggatacc ctactatgta ggcccccctcg ccgggggaaa   1376 ttccagattc gcgtggatga ctcgcaaatc agaagagacc atcactccct ggaacttcga   1436 ggaagtcgtg gataaggggg cctctgccca gtccttcatc gaaaggatga ctaactttga   1496 taaaaatctg cctaacgaaa aggtgcttcc taaacactct ctgctgtacg agtacttcac   1556 agtttataac gagctcacca aggtcaaata cgtcacagaa gggatgagaa agccagcatt   1616 cctgtctgga gagcagaaga agctatcgt ggacctcctc ttcaagacga accggaaagt    1676 taccgtgaaa cagctcaaag aagactattt caaaaagatt gaatgtttcg actctgttga   1736 aatcagcgga gtgaggatc gcttcaacgc atccctggga acgtatcacg atctcctgaa    1796 aatcattaaa gacaaggact tcctggacaa tgaggagaac gaggacattc ttgaggacat   1856
```

```
tgtcctcacc cttacgttgt ttgaagatag ggagatgatt gaagaacgct tgaaaactta    1916
cgctcatctc ttcgacgaca aagtcatgaa acagctcaag aggcgccgat atacaggatg    1976
ggggcggctg tcaagaaaac tgatcaatgg gatccgagac aagcagagtg aaagacaat    2036 cctggatttt cttaagtccg atggatttgc caaccggaac ttcatgcagt tgatccatga    2096
tgactctctc acctttaagg aggacatcca gaaagcacaa gtttctggcc agggggacag    2156
tcttcacgag cacatcgcta atcttgcagg tagcccagct atcaaaaagg gaatactgca    2216
gaccgttaag gtcgtggatg aactcgtcaa agtaatggga aggcataagc ccgagaatat    2276
cgttatcgag atggcccgag agaaccaaac tacccagaag ggacagaaga acagtaggga    2336
aaggatgaag aggattgaag agggtataaa agaactgggg tcccaaatcc ttaaggaaca    2396
cccagttgaa acacccagc ttcagaatga gaagctctac ctgtactacc tgcagaacgg    2456
cagggacatg tacgtggatc aggaactgga catcaatcgg ctctccgact acgacgtgga    2516
tcatatcgtg ccccagtctt ttctcaaaga tgattctatt gataataaag tgttgacaag    2576
atccgataaa aatagaggga agagtgataa cgtcccctca gaagaagttg tcaagaaaat    2636
gaaaaattat tggcggcagc tgctgaacgc caaactgatc acacaacgga agttcgataa    2696
tctgactaag gctgaacgag gtggcctgtc tgagttggat aaagccggct tcatcaaaag    2756
gcagcttgtt gagacacgcc agatcaccaa gcacgtggcc caaattctcg attcacgcat    2816
gaacaccaag tacgatgaaa atgacaaact gattcgagag gtgaaagtta ttactctgaa    2876
gtctaagctg gtctcagatt tcagaaagga ctttcagttt tataaggtga gagagatcaa    2936
caattaccac catgcgcatg atgcctacct gaatgcagtg gtaggcactg cacttatcaa    2996
aaaatatccc aagcttgaat ctgaatttgt ttacggagac tataaagtgt acgatgttag    3056
gaaaatgatc gcaaagtctg agcaggaaat aggcaaggcc accgctaagt acttctttta    3116
cagcaatatt atgaattttt tcaagaccga gattacactg gccaatggag agattcggaa    3176
gcgaccactt atcgaaacaa acggagaaac aggagaaatc gtgtgggaca agggtaggga    3236
tttcgcgaca gtccggaagg tcctgtccat gccgcaggtg aacatcgtta aaaagaccga    3296
agtacagacc ggaggcttct ccaaggaaag tatcctcccg aaaaggaaca gcgacaagct    3356
gatcgcacgc aaaaaagatt gggacccca gaaatacggc ggattcgatt ctcctacagt    3416
cgcttacagt gtactggttg tggccaaagt ggagaaaggg aagtctaaaa aactcaaaag    3476
cgtcaaggaa ctgctgggca tcacaatcat ggagcgatca agcttcgaaa aaaccccat    3536 cgactttctc gaggcgaaag gatataaaga ggtcaaaaaa gacctcatca ttaagcttcc    3596
caagtactct ctctttgagc ttgaaaacgg ccggaaacga atgctcgcta gtgcgggcga    3656
gctgcagaaa ggtaacgagc tggcactgcc ctctaaatac gttaatttct tgtatctggc    3716
cagccactat gaaaagctca agggtctcc cgaagataat gagcagaagc agctgttcgt    3776
ggaacaacac aaacactacc ttgatgagat catcgagcaa ataagcgaat ctccaaaag    3836 agtgatcctc gccgacgcta acctcgataa ggtgctttct gcttacaata agcacaggga    3896
taagcccatc agggagcagg cagaaaacat tatccacttg tttactctga ccaacttggg    3956
cgcgcctgca gccttcaagt acttcgacac caccatagac agaaagcggt acacctctac    4016
aaaggaggtc ctggacgcca cactgattca tcagtcaatt acgggctct atgaaacaag    4076 aatcgacctc tctcagctcg gtggagacag cagggctgac cccaagaaga agaggaaggt    4136
gtga                                                                4140
```

<210> SEQ ID NO 2
<211> LENGTH: 409
<212> TYPE: DNA
<213> ORGANISM: Artificial Sequence
<220> FEATURE:
<223> OTHER INFORMATION: gRNA target sequence with SNR52 promoter and
      SUP4 terminator
<220> FEATURE:
<221> NAME/KEY: CDS
<222> LOCATION: (1)..(6)

<400> SEQUENCE: 2 gcg gcc gcgagctctc tttgaaaaga taatgtatga ttatgctttc actcatattt      56
Ala Ala
1 atacagaaac ttgatgtttt ctttcgagta tatacaaggt gattacatgt acgtttgaag   116 tacaactcta gattttgtag tgccctcttg ggctagcggt aaaggtgcgc attttttcac   176 accctacaat gttctgttca aaagattttg gtcaaacgct gtagaagtga aagttggtgc   236 gcatgtttcg gcgttcgaaa cttctccgca gtgaaagata aatgatcgag taaaaaattg   296 tacttgggtt ttagagctag aaatagcaag ttaaaataag gctagtccgt tatcaacttg   356 aaaaagtggc accgagtcgg tggtgctttt tttgttttttt atgtctggta ccg         409

<210> SEQ ID NO 3
<211> LENGTH: 252
<212> TYPE: DNA
<213> ORGANISM: Artificial Sequence
<220> FEATURE:
<223> OTHER INFORMATION: Mature peptide of human parathyroid homone
<220> FEATURE:
<221> NAME/KEY: CDS
<222> LOCATION: (1)..(6)

<400> SEQUENCE: 3 tct gtg agtgaaatac agcttatgca taacctggga aaacatctga actcgatgga      56
Ser Val
1 gagagtagaa tggctgagta agaagctgca ggatgtgcac aattttgttg cccttggagc   116 tcctctagct cccagagatg ctggttccca gaggccccga aaaaaggaag acaatgtctt   176 ggttgagagc catgaaaaaa gtcttggaga ggcagacaaa gctggtgtga atgtattaac   236 taaagctaaa tcccag                                                   252

<210> SEQ ID NO 4
<211> LENGTH: 684
<212> TYPE: DNA
<213> ORGANISM: Artificial Sequence
<220> FEATURE:
<223> OTHER INFORMATION: engineered version pf UKG
<220> FEATURE:
<221> NAME/KEY: CDS
<222> LOCATION: (1)..(6)

<400> SEQUENCE: 4 atg gtc agtgtcatca aagaagaaat gaagatcaag ttgcacatgg aaggtaacgt      56
Met Val
1 taatggtcat gcctttgtta ttgaaggtga tggtaaaggt aaaccatacg atggtactca   116 aactttgaac ttgactgtca agaaggtgc tccattgcca ttctcttacg atattttgac    176 taacgccttc caatacggta atagagcttt tactaagtac ccagccgata tcccagatta   236 ctttaagcaa acttttccag aaggttactc ctgggaaaga actatgtctt acgaagataa   296

```
cgctatctgc aacgtcagat ccgaaatttc tatggaaggt gattgcttca tctacaagat    356
cagattcgat ggtaagaact tccaccaaa tggtccagtc atgcaaaaaa agactttgaa    416
gtgggaacca tccaccgaaa tgatgtatgt tagagatggt ttcttgatgg gtgatgtcaa    476
tatggctttg ttgttggaag gtggtggtca tcatagatgt gatttcaaga cttcttacaa    536
ggccaagaag gttgttcaat tgccagatgc tcataagatc gatcacagaa tcgaaatctt    596
gtcccacgat agagattact ccaaggttaa gttgtacgaa aacgctgttg ctagaaactc    656
tttgttgcca tctcaagctt ctaagtaa                                      684

<210> SEQ ID NO 5
<211> LENGTH: 60
<212> TYPE: DNA
<213> ORGANISM: Artificial Sequence
<220> FEATURE:
<223> OTHER INFORMATION: Equine rhinitis B virus 2A peptide
<220> FEATURE:
<221> NAME/KEY: misc_structure
<222> LOCATION: (1)..(6)

<400> SEQUENCE: 5
ggggcgacaa atttcagttt gctaaagcta gcgggcgatg tagaacttaa tcctggtcct    60

<210> SEQ ID NO 6
<211> LENGTH: 6721
<212> TYPE: DNA
<213> ORGANISM: Artificial Sequence
<220> FEATURE:
<223> OTHER INFORMATION: Plasmid 1
<220> FEATURE:
<221> NAME/KEY: CDS
<222> LOCATION: (1)..(6)

<400> SEQUENCE: 6 gcg atc gcggctcccg acatcttgga ccattagctc cacaggtatc ttcttccctc    56
Ala Ile
 1 tagtggtcat aacagcagct tcagctacct ctcaatttca atcgttgcgt tacacacaca   116 aaaaccaac acacatccat cttcgatgga tagcgatttt attatctaac tgctgatcga   176 gtgtagccag atctcaatgc atactttgta cgttcaaaat acaatgcagt agatatattt   236 atgcatatta catataatac atatcacata ggaagcaaca ggcgcgttgg acttttaatt   296 ttcgaggacc gcgaatcctt acatcacacc caatccccca caagtgatcc cccacacacc   356 atagcttcaa aatgtttcta ctccttttt actcttccag attttctcgg actccgcgca   416 tcgccgtacc acttcaaaac acccaagcac agcatactaa atttcccctc tttcttcctc   476 tagggtgtcg ttaattaccc gtactaaagg tttggaaaag aaaaaagaga ccgcctcgtt   536 tctttttctt cgtcgaaaaa ggcaataaaa attttttatca cgtttctttt tcttgaaaat   596 tttttttttt gattttttc tctttcgatg acctcccatt gatatttaag ttaataaacg   656 gtcttcaatt tctcaagttt cagtttcatt tttcttgttc tattacaact ttttttactt   716 cttgctcatt agaaagaaag catagcaatc taatctaagt tttaattaca aaagatcttt   776 gtcgatccta ccatccactc gacacacccg ccagcggccg ctgccaagct tccgagctct   836 cgaattcaaa ggaggtacca accatggcgg taccttgcga tatctacctc gaggtttcta   896 gaagttgtct cctcctgcac tgactgactg atacaatcga tttctggatc cgcaggcctc   956 tgctagcttg actgactgag atacagcgta ccttcagctc atcatgtaat tagttatgtc  1016
```

-continued

```
acgcttacat tcacgccctc cccccacatc cgctctaacc gaaaaggaag gagttagaca    1076
acctgaagtc taggtcccta tttatttttt tatagttatg ttagtattaa gaacgttatt    1136
tatatttcaa attttctttt tttttctgta cagacgcgtg tacgcatgta acattatact    1196
gaaaaccttg cttgagaagg ttttgggacg ctcgaaggct ttaatttgcg gccaaagcaa    1256
gtaaaacctc tacaaatgtg gtattggccc atctctatcg gtatcgtagc ataacccctt    1316
ggggcctcta acgggtctt gagggttttt ttgtgcccct cgggccggat tgctatctac     1376
cggcattggc gcagaaaaaa atgcctgatg cgacgctgcg cgtcttatac tcccacatat    1436
gccagattca gcaacggata cggcttcccc aacttgccca cttccatacg tgtcctcctt    1496
accagaaatt tatccttaag gtcgtcagct atcctgcagg tcaattcatc atttttttt     1556 tattctttt tttgatttcg gtttctttga aattttttg attcggtaat ctccgaacag      1616
aaggaagaac gaaggaagga gcacagactt agattggtat atatacgcat atgtagtgtt    1676
gaagaaacat gaaattgccc agtattctta acccaactgt acagaacaaa aacctgcaga    1736
aaacgaagat aaatcatgtc gaaagctaca tataaggaac gtgctgctac tcatcctagt    1796
cctgttgctg ccaagctatt taatatcatg cacgaaaagc aaacaaactt gtgtgcttca    1856
ttggatgttc gtaccaccaa ggaattactg gagttagttg aagcattagg tcccaaaatt    1916
tgtttactaa aaacacatgt ggatattttg actgattttt ctatggaggg cacagttaag    1976
ccgctaaagg cattatccgc caagtacaat ttttactct tcgaagacag aaaatttgct     2036
gacattggta atacagtcaa attgcagtac tctgcgggtg tatacagaat agcagaatgg    2096
gcagacatta cgaatgcaca cggtgtggtg ggcccaggta ttgttagcgg tttgaagcag    2156
gcggcagaag aagtaacaaa ggaacctaga ggtcttttga tgttagcaga attgtcatgc    2216
aagggctccc tatctactgg agaatatact aagggtactg ttgacattgc gaagagcgac    2276
aaagattttg ttatcggctt tattgctcaa agagacatgg gtggaagaga tgaaggttac    2336
gattggttga ttatgacacc cggtgtgggt ttagatgaca agggagacgc attgggtcaa    2396
cagtatagaa ccgtggatga tgtggtctct acaggatctg acattattat tgttggaaga    2456
ggactatttg caagggaag ggatgctaag gtagaggtg aacgttacag aaaagcaggc      2516
tgggaagcat atttgagaag atgcggccag caaaactaaa aaactgtatt ataagtaaat    2576
gcatgtatac taaactcaca aattagagct tcaatttaat tatatcagtt attccccct    2636 gcaggcgatc tctcgatttc gatcaagaca ttcctttaat ggtcttttct ggacaccact    2696
aggggtcaga agtagttcat caaacttttct tccctcccta atctcattgg ttaccttggg   2756
ctatcgaaac ttaattaacc agtcaagtca gctacttggc gagatcgact tgtctgggtt    2816
tcgactacgc tcagaattgc gtcagtcaag ttcgatctgg tccttgctat tgcacccgtt    2876
ctccgattac gagtttcatt taaatcatgt gagcaaaagg ccagcaaaag gccaggaacc    2936
gtaaaaaggc cgcgttgctg gcgttttttcc ataggctccg ccccctgac gagcatcaca    2996 aaaatcgacg ctcaagtcag aggtggcgaa acccgacagg actataaaga taccaggcgt    3056
ttccccctgg aagctccctc gtgcgctctc ctgttccgac cctgccgctt accggatacc    3116
tgtccgcctt tctcccttcg ggaagcgtgg cgctttctca tagctcacgc tgtaggtatc    3176
tcagttcggt gtaggtcgtt cgctccaagc tgggctgtgt gcacgaaccc cccgttcagc    3236
ccgaccgctg cgccttatcc ggtaactatc gtcttgagtc caacccggta agacacgact    3296
tatcgccact ggcagcagcc actggtaaca ggattagcag agcgaggtat gtaggcggtg    3356
ctacagagtt cttgaagtgg tggcctaact acggctacac tagaagaaca gtatttggta    3416
```

```
tctgcgctct gctgaagcca gttaccttcg gaaaaagagt tggtagctct tgatccggca   3476
aacaaaccac cgctggtagc ggtggttttt ttgtttgcaa gcagcagatt acgcgcagaa   3536
aaaaaggatc tcaagaagat cctttgatct tttctacggg gtctgacgct cagtggaacg   3596
aaaactcacg ttaagggatt ttggtcatga gattatcaaa aaggatcttc acctagatcc   3656
ttttaaatta aaaatgaagt tttaaatcaa tctaaagtat atatgagtaa acttggtctg   3716
acagttacca atgcttaatc agtgaggcac ctatctcagc gatctgtcta tttcgttcat   3776
ccatagttgc atttaaattt ccgaactctc caaggccctc gtcggaaaat cttcaaacct   3836
ttcgtccgat ccatcttgca ggctacctct cgaacgaact atcgcaagtc tcttggccgg   3896
ccttgcgcct tggctattgc ttggcagcgc ctatcgccag gtattactcc aatcccgaat   3956
atccgagatc gggatcaccc gagagaagtt caacctacat cctcaatccc gatctatccg   4016
agatccgagg aatatcgaaa tcgggcgcg ccaacgaagc atctgtgctt cattttgtag   4076 aacaaaatg caacgcgaga gcgctaattt ttcaaacaaa gaatctgagc tgcatttta   4136 cagaacagaa atgcaacgcg aaagcgctat tttaccaacg aagaatctgt gcttcatttt   4196
tgtaaaacaa aaatgcaacg cgagagcgct aattttttcaa acaaagaatc tgagctgcat   4256
ttttacagaa cagaaatgca acgcgagagc gctatttttac caacaaagaa tctatacttc   4316 tttttttgttc tacaaaaatg catcccgaga gcgctatttt tctaacaaag catcttagat   4376
tacttttttt ctcctttgtg cgctctataa tgcagtctct tgataacttt ttgcactgta   4436
ggtccgttaa ggttagaaga aggctacttt ggtgtctatt ttctcttcca taaaaaaagc   4496
ctgactccac ttcccgcgtt tactgattac tagcgaagct gcgggtgcat tttttcaaga   4556
taaaggcatc cccgattata ttctataccg atgtggattg cgcatacttt gtgaacagaa   4616
agtgatagcg ttgatgattc ttcattggtc agaaaattat gaacggtttc ttctattttg   4676
tctctatata ctacgtatag gaaatgttta cattttcgta ttgttttcga ttcactctat   4736
gaatagttct tactacaatt ttttgtcta aagagtaata ctagagataa acataaaaaa   4796
tgtagaggtc gagtttagat gcaagttcaa ggagcgaaag gtggatgggt aggttatata   4856
gggatatagc acagagatat atagcaaaga gatacttttg agcaatgttt gtggaagcgg   4916
tattcgcaat attttagtag ctcgttacag tccggtgcgt ttttggtttt ttgaaagtgc   4976
gtcttcagag cgcttttggt tttcaaaagc gctctgaagt tcctatactt cctagagaat   5036
aggaacttcg gaataggaac ttcaaagcgt ttccgaaaac gagcgcttcc gaaaatgcaa   5096
cgcgagctgc gcacatacag ctcactgttc acgtcgcacc tatatctgcg tgttgcctgt   5156
atatatatat acatgagaag aacggcatag tgcgtgttta tgcttaaatg cgtacttata   5216
tgcgtctatt tatgtaggat gaaaggtagt ctagtacctc ctgtgatatt atcccattcc   5276
atgcggggta tcgtatgctt ccttcagcac tacccttttag ctgttctata tgctgccact   5336
cctcaattgg attagtctca tccttcaatg ctatcatttc ctttgatatt ggatcatacg   5396
gcgcgcctgg tgtaccgaga acgatcctct cagtgcgagt ctcgacgatc catatcgttg   5456
cttggcagtc agccagtcgg aatccagctt gggacccagg aagtccaatc gtcagatatt   5516
gtactcaagc ctggtcacgg cagcgtaccg atctgtttaa acctagatat tgatagtctg   5576
atcggtcaac gtataatcga gtcctagctt ttgcaaacat ctatcaagag acaggatcag   5636
caggaggctt tcgcatgatt gaacaagatg gattgcacgc aggttctccg gccgcttggg   5696
tggagaggct attcggctat gactgggcac aacagacaat cggctgctct gatgccgccg   5756
```

```
tgttccggct gtcagcgcag gggcgtccgg ttcttttttgt caagaccgac ctgtccggtg      5816
ccctgaatga actgcaagac gaggcagcgc ggctatcgtg gctggcgacg acgggcgttc      5876
cttgcgcggc tgtgctcgac gttgtcactg aagcgggaag ggactggctg ctattgggcg      5936
aagtgccggg gcaggatctc ctgtcatctc accttgctcc tgccgagaaa gtatccatca      5996
tggctgatgc aatgcggcgg ctgcatacgc ttgatccggc tacctgccca ttcgaccacc      6056
aagcgaaaca tcgcatcgag cgagcacgta ctcggatgga agccggtctt gtcgatcagg      6116
atgatctgga cgaagagcat caggggctcg cgccagccga actgttcgcc aggctcaagg      6176
cgtctatgcc cgacggcgag gatctcgtcg tgacccacgg cgatgcctgc ttgccgaata      6236
tcatggtgga aaatggccgc ttttctggat tcatcgactg tggccgtctg ggtgtggcgg      6296
accgctatca ggacatagcg ttggctaccc gtgatattgc tgaagagctt ggcggcgaat      6356
gggctgaccg cttccttgtg ctttacggta tcgccgcgcc cgattcgcag cgcatcgcct      6416
tctatcgcct tcttgacgag ttcttctgac cgattctagg tgcattggcg cagaaaaaaa      6476
tgcctgatgc gacgctgcgc gtcttatact cccacatatg ccagattcag caacggatac      6536
ggcttcccca acttgcccac ttccatacgt gtcctcctta ccagaaattt atccttaagg      6596
tcgtttaaac tcgactctgg ctctatcgaa tctccgtcgt ttcgagctta cgcgaacagc      6656
cgtggcgctc atttgctcgt cgggcatcga atctcgtcag ctatcgtcag cttacctttt      6716
tggca                                                                  6721
```

<210> SEQ ID NO 7
<211> LENGTH: 6217
<212> TYPE: DNA
<213> ORGANISM: Artificial Sequence
<220> FEATURE:
<223> OTHER INFORMATION: Plasmid 2
<220> FEATURE:
<221> NAME/KEY: CDS
<222> LOCATION: (1)..(6)

<400> SEQUENCE: 7

```
cag cga catggaggcc cagaataccc tccttgacag tcttgacgtg cgcagctcag            56
Gln Arg
1 gggcatgatg tgactgtcgc ccgtacattt agcccataca tccccatgta taatcatttg       116 catccataca ttttgatggc cgcacggcgc gaagcaaaaa ttacggctcc tcgctgcgga       176 cctgcgagca gggaaacgct cccctcacag acgcgttgaa ttgtcccac gccgcgcccc         236 tgtagagaaa tataaaaggt taggatttgc cactgaggtt cttctttcat atacttcctt      296 ttaaaatctt gctaggatac agttctcaca tcacatccga acataaacaa ccatgggtaa       356 aaagcctgaa ctcaccgcga cgtctgtcga agagtttctg atcgaaaagt tcgacagcgt      416 ctccgacctg atgcagctct cggagggcga agaatctcgt gctttcagct tcgatgtagg      476 agggcgtgga tatgtcctgc gggtaaatag ctgcgccgat ggtttctaca agatcgtta       536 tgtttatcgg cactttgcat cggccgcgct cccgattccg gaagtgcttg acattgggga      596 attcagcgag agcctgacct attgcatctc ccgccgtgca cagggtgtca cgttgcaaga      656 cctgcctgaa accgaactgc ccgctgttct gcagccggtc gcggaggcca tggatgcgat      716 cgctgcggcc gatcttagcc agacgagcgg gttcggccca ttcggaccgc aaggaatcgg      776 tcaatacact acatggcgtg atttcatatg cgcgattgct gatccccatg tgtatcactg      836 gcaaactgtg atggacgaca ccgtcagtgc gtccgtcgcg caggctctcg atgagctgat      896
```

```
gctttgggcc gaggactgcc ccgaagtccg gcacctcgtg cacgcggatt tcggctccaa    956
caatgtcctg acggacaatg gccgcataac agcggtcatt gactggagcg aggcgatgtt   1016
cggggattcc caatacgagg tcgccaacat cttcttctgg aggccgtggt tggcttgtat   1076
ggagcagcag acgcgctact tcgagcggag gcatccggag cttgcaggat cgccgcggct   1136
ccgggcgtat atgctccgca ttggtcttga ccaactctat cagagcttgg ttgacggcaa   1196
tttcgatgat gcagcttggg cgcagggtcg atgcgacgca atcgtccgat ccggagccgg   1256
gactgtcggg cgtacacaaa tcgcccgcag aagcgcggcc gtctggaccg atggctgtgt   1316
agaagtactc gccgatagtg gaaaccgacg ccccagcact cgtccgaggg caaaggaata   1376
atctcgagtc atgtaattag ttatgtcacg cttacattca cgccctcccc ccacatccgc   1436
tctaaccgaa aaggaaggag ttagacaacc tgaagtctag gtccctattt atttttttat   1496
agttatgtta gtattaagaa cgttatttat atttcaaatt tttctttttt ttctgtacag   1556
acgcgtgtac gcatgtaaca ttatactgaa aaccttgctt gagaaggttt tgggacggcg   1616
gtgtgaaata ccgcacagat gcgtaaggag aaaataccgc atcaggaaat tgtaaacgtt   1676
aatattttgt taaaattcgc gttaaatttt tgttaaatca gctcattttt taaccaatag   1736
gccgaaatcg gcaaaatccc ttataaatca aagaataga ccgagatagg gttgagtgtt   1796
gttccagttt ggaacaagag tccactatta agaacgtgg actccaacgt caaagggcga   1856
aaaaccgtct atcagggcga tggcccacta cgtgaaccat caccctaatc aagttttttg   1916
gggtcgaggt gccgtaaagc actaaatcgg aaccctaaag ggagccccg atttagagct   1976
tgacggggaa agccggcgaa cgtggcgaga aggaaggga agaaagcgaa aggagcgggc   2036
gctagggcgc tggcaagtgt agcggtcacg ctgcgcgtaa ccaccacacc cgccgcgctt   2096
aatgcgccgc tacagggcgc gtcgcgccat tcgccattca ggctgcgcaa ctgttgggaa   2156
gggcgatcgg tgcgggcctc ttcgctatta cgccagctgg cgaaagggg atgtgctgca   2216
aggcgattaa gttgggtaac gccagggttt cccagtcac gacgttgtaa acgacggcc   2276
agtgagcgcg cgtaatacga ctcactatag ggcgaattgg gtaccgggcc ccccctcgag   2336
gtcgacggta tcgataagct tgatatcgaa ttcctgcagc ccggggggatc cactagttct   2396
agagcggccg ccaccgcggt ggagctccag cttttgttcc ctttagtgag ggttaattgc   2456
gcgcttggcg taatcatggt catagctgtt tcctgtgtga aattgttatc cgctcacaat   2516
tccacacaac ataggagccg gaagcataaa gtgtaaagcc tggggtgcct aatgagtgag   2576
gtaactcaca ttaattgcgt tgcgctcact gcccgctttc cagtcgggaa acctgtcgtg   2636
ccagctgcat taatgaatcg gccaacgcgc ggggagaggc ggtttgcgta ttgggcgctc   2696
ttccgcttcc tcgctcactg actcgctgcg ctcggtcgtt cggctgcggc gagcggtatc   2756
agctcactca aaggcggtaa tacggttatc cacagaatca ggggataacg caggaaagaa   2816
catgtgagca aaaggccagc aaaaggccag gaaccgtaaa aaggccgcgt tgctggcgtt   2876
tttccatagg ctccgccccc ctgacgagca tcacaaaaat cgacgctcaa gtcagaggtg   2936
gcgaaacccg acaggactat aaagatacca ggcgtttccc cctggaagct ccctcgtgcg   2996
ctctcctgtt ccgaccctgc cgcttaccgg atacctgtcc gcctttctcc cttcgggaag   3056
cgtggcgctt tctcatagct cacgctgtag gtatctcagt tcggtgtagg tcgttcgctc   3116
caagctgggc tgtgtgcacg aaccccccgt tcagcccgac cgctgcgcct tatccggtaa   3176
ctatcgtctt gagtccaacc cggtaagaca cgacttatcg ccactggcag cagccactgg   3236
taacaggatt agcagagcga ggtatgtagg cggtgctaca gagttcttga agtggtggcc   3296
```

```
taactacggc tacactagaa ggacagtatt tggtatctgc gctctgctga agccagttac   3356
cttcggaaaa agagttggta gctcttgatc cggcaaacaa accaccgctg gtagcggtgg   3416 ttttttgtt  tgcaagcagc agattacgcg cagaaaaaaa ggatctcaag aagatccttt   3476
gatcttttct acggggtctg acgctcagtg gaacgaaaac tcacgttaag ggattttggt   3536
catgagatta tcaaaaagga tcttcaccta gatcctttta aattaaaaat gaagttttaa   3596
atcaatctaa agtatatatg agtaaacttg gtctgacagt taccaatgct taatcagtga   3656
ggcacctatc tcagcgatct gtctatttcg ttcatccata gttgcctgac tccccgtcgt   3716
gtagataact acgatacggg agggcttacc atctggcccc agtgctgcaa tgataccgcg   3776
agacccacgc tcaccggctc cagatttatc agcaataaac cagccagccg gaagggccga   3836
gcgcagaagt ggtcctgcaa ctttatccgc ctccatccag tctattaatt gttgccggga   3896
agctagagta agtagttcgc cagttaatag tttgcgcaac gttgttgcca ttgctacagg   3956
catcgtggtg tcacgctcgt cgtttggtat ggcttcattc agctccggtt cccaacgatc   4016
aaggcgagtt acatgatccc ccatgttgtg caaaaaagcg gttagctcct tcggtcctcc   4076
gatcgttgtc agaagtaagt tggccgcagt gttatcactc atggttatgg cagcactgca   4136
taattctctt actgtcatgc catccgtaag atgcttttct gtgactggtg agtactcaac   4196
caagtcattc tgagaatagt gtatgcggcg accgagttgc tcttgcccgg cgtcaatacg   4256
ggataatacc gcgccacata gcagaacttt aaaagtgctc atcattggaa aacgttcttc   4316
ggggcgaaaa ctctcaagga tcttaccgct gttgagatcc agttcgatgt aacccactcg   4376
tgcacccaac tgatcttcag catctttta  tttcaccagc gtttctgggt gagcaaaaac   4436
aggaaggcaa aatgccgcaa aaagggaat aagggcgaca cggaaatgtt gaatactcat   4496
actcttcctt tttcaatatt attgaagcat ttatcagggt tattgtctca tgagcggata   4556
catatttgaa tgtatttaga aaataaaca  aataggggtt ccgcgcacat ttccccgaaa   4616
agtgccacct gaacgaagca tctgtgcttc attttgtaga acaaaaatgc aacgcgagag   4676
cgctaatttt tcaaacaaag aatctgagct gcatttttac agaacagaaa tgcaacgcga   4736
aagcgctatt ttaccaacga agaatctgtg cttcattttt gtaaacaaa  aatgcaacgc   4796 gagagcgcta attttcaaa  caaagaatct gagctgcatt tttacagaac agaaatgcaa   4856
cgcgagagcg ctattttacc aacaaagaat ctatacttct tttttgttct acaaaaatgc   4916
atcccgagag cgctattttt ctaacaaagc atcttagatt actttttttc tcctttgtgc   4976
gctctataat gcagtctctt gataactttt tgcactgtag gtccgttaag gttagaagaa   5036
ggctactttg gtgtctattt tctcttccat aaaaaaagcc tgactccact tcccgcgttt   5096
actgattact agcgaagctg cgggtgcatt ttttcaagat aaaggcatcc ccgattatat   5156
tctataccga tgtggattgc gcatactttg tgaacagaaa gtgatagcgt tgatgattct   5216
tcattggtca gaaaattatg aacggtttct tctatttgt  ctctatatac tacgtatagg   5276
aaatgtttac attttcgtat tgttttcgat tcactctatg aatagttctt actacaattt   5336
ttttgtctaa agagtaatac tagagataaa cataaaaaat gtagaggtcg agtttagatg   5396
caagttcaag gagcgaaagg tggatgggta ggttatatag ggatatagca cagagatata   5456
tagcaaagag atacttttga gcaatgtttg tggaagcggt attcgcaata ttttagtagc   5516
tcgttacagt ccggtgcgtt tttggttttt tgaaagtgcg tcttcagagc gcttttggtt   5576
ttcaaaagcg ctctgaagtt cctatacttt ctagagaata ggaacttcgg aataggaact   5636
```

```
tcaaagcgtt tccgaaaacg agcgcttccg aaaatgcaac gcgagctgcg cacatacagc    5696
tcactgttca cgtcgcacct atatctgcgt gttgcctgta tatatatata catgagaaga    5756
acggcatagt gcgtgtttat gcttaaatgc gtacttatat gcgtctattt atgtaggatg    5816
aaaggtagtc tagtacctcc tgtgatatta tcccattcca tgcggggtat cgtatgcttc    5876
cttcagcact acccctttagc tgttctatat gctgccactc ctcaattgga ttagtctcat    5936
ccttcaatgc tatcatttcc tttgatattg gatcatacta agaaaccatt attatcatga    5996
cattaaccta taaaaatagg cgtatcacga ggccctttcg tctcgcgcgt ttcggtgatg    6056
acggtgaaaa cctctgacac atgcagctcc cggagacggt cacagcttgt ctgtaagcgg    6116
atgccgggag cagacaagcc cgtcagggcg cgtcagcggg tgttggcggg tgtcggggct    6176
ggcttaacta tgcggcatca gagcagattg tactgagagt g                        6217
```

<210> SEQ ID NO 8
<211> LENGTH: 1293
<212> TYPE: DNA
<213> ORGANISM: Artificial Sequence
<220> FEATURE:
<223> OTHER INFORMATION: Fusion protein of yeast alpha mating factor-
      parathyroid hormone-2A peptide and UKG florescence protein
<220> FEATURE:
<221> NAME/KEY: CDS
<222> LOCATION: (1)..(6)

<400> SEQUENCE: 8

```
cgg ccg aaaaaaatga gatttccttc aattttttact gctgttttat tcgcagcatc         56
Arg Pro
  1 ctccgcatta gctgctccag tcaacactac aacagaagat gaaacggcac aaattccggc    116 tgaagctgtc atcggttact cagatttaga aggggatttc gatgttgctg ttttgccatt    176 ttccaacagc acaaataacg ggttattgtt tataaatact actattgcca gcattgctgc    236 taaagaagaa ggggtatctc tcgagaaaag agaggctgaa gcttctgtga gtgaaataca    296 gcttatgcat aacctgggaa aacatctgaa ctcgatggag agagtagaat ggctgagtaa    356 gaagctgcag gatgtgcaca ttttgttgc ccttggagct cctctagctc ccagagatgc    416 tggttcccag aggccccgaa aaaggaaga caatgtcttg gttgagagcc atgaaaaaag    476 tcttggagag gcagacaaag ctggtgtgaa tgtattaact aaagctaaat cccagggggc    536 gacaaatttc agtttgctaa agctagcggg cgatgtagaa cttaatcctg gtcctgtcga    596 catggtcagt gtcatcaaag aagaaatgaa gatcaagttg cacatggaag gtaacgttaa    656 tggtcatgcc tttgttattg aaggtgatgg taaaggtaaa ccatacgatg gtactcaaac    716 tttgaacttg actgtcaaag aaggtgctcc attgccattc tcttacgata ttttgactaa    776 cgccttccaa tacggtaata gagctttac taagtaccca gccgatatcc cagattactt    836 taagcaaact tttccagaag gttactcctg ggaaagaact atgtcttacg aagataacgc    896 tatctgcaac gtcagatccg aaatttctat ggaaggtgat tgcttcatct acaagatcag    956 attcgatggt aagaactttc caccaaatgg tccagtcatg caaaaaaaga ctttgaagtg    1016 ggaaccatcc accgaaatga tgtatgttag agatggtttc ttgatgggtg atgtcaatat    1076 ggctttgttg ttggaaggtg gtggtcatca tagatgtgat ttcaagactt cttacaaggc    1136 caagaaggtt gttcaattgc cagatgctca taagatcgat cacagaatcg aaatcttgtc    1196 ccacgataga gattactcca aggttaagtt gtacgaaaac gctgttgcta gaaactcttt    1256 gttgccatct caagcttcta agtaagaatt cggtacc                             1293
```

```
<210> SEQ ID NO 9
<211> LENGTH: 267
<212> TYPE: DNA
<213> ORGANISM: Artificial Sequence
<220> FEATURE:
<223> OTHER INFORMATION: Saccharomyces cerevisiae alpha mating factor
      peptide mature sequence
<220> FEATURE:
<221> NAME/KEY: gene
<222> LOCATION: (1)..(6)

<400> SEQUENCE: 9
atgagatttc cttcaatttt tactgctgtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacgggttat tgtttataaa tactactatt gccagcattg ctgctaaaga agaagggta      240 tctctcgaga aaagagaggc tgaagct                                         267
```